United States Patent [19]

Kambara et al.

[11] Patent Number: 4,832,815
[45] Date of Patent: May 23, 1989

[54] WAVELENGTH DISPERSION ELECTROPHORESIS APPARATUS

[75] Inventors: Hideki Kambara, Hachiouji; Yoshitoshi Ito, Oume, both of Japan

[73] Assignee: Hitachi, Ltd., Tokyo, Japan

[21] Appl. No.: 259,311

[22] Filed: Oct. 18, 1988

[30] Foreign Application Priority Data

Oct. 30, 1987 [JP] Japan .................... 62-272945

[51] Int. Cl.$^4$ .................................... G01N 27/26
[52] U.S. Cl. ........................ 204/299 R; 204/182.8; 356/344
[58] Field of Search ............ 204/182.8, 299 R, 180.1; 356/344

[56] References Cited
PUBLICATIONS

Smith, L. M. et al., "Fluorescence Detection in Automated DNA Sequence Analysis" Nature vol. 321 (Jun. 12, 1986) pp. 674–679.

Primary Examiner—John F. Niebling
Assistant Examiner—John S. Starsiak, Jr.
Attorney, Agent, or Firm—Antonelli, Terry & Wands

[57] ABSTRACT

In a wavelength dispersion electrophoresis apparatus which detects fluorescences of unequal wavelengths emitted from the samples of DNA, RNA or the like labeled with a plurality of fluorophores, a direct-vision prism (14) is interposed between a two-dimensional fluorescence detector (7) and an electrophoretic plate (17) in order to separate and discriminate the emission wavelengths of the respective fluorophores. The direct-vision prism (14) is disposed for the wavelength dispersion of the fluorescences in this manner, whereby the fluorescences of the individual wavelengths can be separated and detected at a high sensitivity by a simple mechanism and without distorting a fluorescence image.

5 Claims, 3 Drawing Sheets

4,832,815

WAVELENGTH DISPERSION ELECTROPHORESIS APPARATUS

BACKGROUND OF THE INVENTION

The present invention relates to an electrophoresis apparatus for separatingly detecting DNA, RNA or the like, and more particularly to a wavelength dispersion electrophoresis apparatus which is well suited for detecting fluorescences from a sample labeled with a plurality of fluorophores having unequal wavelengths.

Heretofore, the determination of a base sequence on DNA has been performed in such a way that a separation pattern is transferred on a photograph by the use of autoradiography. However, there has been the difficulty that labor and time are expended besides the troublesome handling of radioactive elements. Therefore, note is taken of a system wherein a DNA fragment during electrophoresis separation is detected in real time through the fluorescence labeling of the DNA (L. M. Smith et al; Nature, Vol. 321, pp. 674–679 (1986)). With this method, while the specified end of the DNA is maintained, the fluorescence labeling is done at the other end or halfway so as to prepare four kinds of DNA fragment groups in each of which a base possessed by a nucleic acid at the other end is adenine (A), cytosine (C), thymine (T) or guanine (G). At this time, fluorophores of unequal emission wavelengths are used for labeling the respective base species. The four fragment groups are put together, and are subjected to the electrophoresis gel separation. The electrophoretic migration speed is higher for a shorter DNA fragment. Therefore, when a place at a fixed distance from a sample inlet is irradiated by a laser, the fragments pass through the irradiated region and give forth fluorescences successively from the shortest fragment. Since the emission wavelengths differ depending upon the base species, the base species are determined from the wavelengths. The lengths of the fragments can be determined from the migration times.

In order to discriminate the four kinds of fluorescences of unequal wavelengths, L. M. Smith et al rotate four sorts of filters of unequal transmission wavelengths by way of example. Besides, an apparatus which employs a flat plate type gel in order to permit the measurements of a plurality of samples is sold by Applied Biosystems Inc. in U.S. In this apparatus, a laser beam is fined to irradiate one point of a gel plane. Fluorescence emitted from here passes through a rotary filter, and is detected by a photosensitive portion. In measuring a large number of samples, information items are obtained in such a way that the gel plane is scanned on one straight line by interlocking laser irradiation positions and the detecting portion.

In the prior art employing the rotary filter, it has not been considered to increase the amount of the fluorescence which is received by the detecting portion. More specifically, when it is intended to detect the region of the surface of an electrophoretic plate in a range of 10 cm in a horizontal direction (a direction orthogonal to the direction of the electrophoresis), the period of time for which the laser irradiates each spot becomes 1/200 of one scanning time (usually, 1 second or so), assuming the width of the laser beam to be 0.5 mm. Moreover, since four filters rotate in correspondence with the four base species, the measurement period of time for one base species noticed is further quartered. Eventually, only about 1/800 of the whole measurement period of time is used for the measurement of one base species at one spot, so that a high sensitivity is not attained due to a small amount of fluorescence received.

SUMMARY OF THE INVENTION

An object of the present invention is to provide a wavelength dispersion electrophoresis apparatus of high sensitivity in which fluorescences of respective wavelengths can be received over the whole measurement period of time by a simple mechanism without employing a rotary filter.

In order to accomplish the above object, the wavelength dispersion electrophoresis apparatus of the present invention is so constructed that a measurement region (namely, a range covering a fixed distance in a horizontal direction at a predetermined distance from the electrophoresis start point of an electrophoretic plate) is simultaneously irradiated with a light beam, that the wavelength dispersion of emitted fluorescence is induced by a direct-vision prism (namely, a composite prism in which a plurality of unit prisms made of different materials are combined, and which renders the deflection of the D-line almost zero and disperses the other lines on both the sides thereof), that the wavelength dispersion is focused on an image intensifier by a lens system, and that the focused image is detected by a two-dimensional detector.

That is, the wavelength dispersion electrophoresis apparatus of the present invention accomplishes the object thereof in such a way that the direct-vision prism is disposed in front of a condensing lens for condensing the fluorescence (between the condensing lens and the electrophoretic plate), thereby making it possible to perform the wavelength dispersion and the focusing of the dispersed fluorescence at the same time.

More concretely, in an electrophoresis apparatus having means for electrophoretically separating s sample group which consists of samples labeled with at least two kinds of fluorophores, excitation means for exciting the fluorophore which has labeled the sample, thereby causing it to emit fluorescence, and detection means for detecting the emitted fluorescence; the wavelength dispersion electrophoresis apparatus of the present invention consists in that a direct-vision prism which disperses the fluorescences at respective fluorescence wavelengths thereof is disposed in front of said detection means.

In more detail, the wavelength dispersion electrophoresis apparatus of the present invention can be typically constructed as follows: (i) The electrophoresis separation means is configured of a plurality of migration lanes which are set in parallel, (ii) said excitation means is means for forming excitation light which intersects all of said migration lanes and which enters perpendicularly to said migration lanes, (iii) said detection means is constructed of a two-dimensional detector, and (iv) said direct-vision prism and said detection means are so arranged that a fluorescence image undergoes the wavelength dispersion in a vertical direction (in a migration direction).

Usually, a laser beam is employed as the excitation light. Typically, the laser beam can be set as a collimated beam whose section in the measurement region is substantially circular and has a diameter of 0.3 mm or less.

The wavelength differences among the plurality of fluorescence labels and the angular dispersion of the direct-vision prism are desirably set so that fluorescence images based on the different kinds of fluorophores may be spaced at least 0.1 mm on the image intensifier. The reason is that a positional resolution for the fluorescence images on a present-day fluorescence detector including the image intensifier is 0.03-0.05 mm.

Besides, a filter for cutting the exciting laser beam is usually disposed in front of the direct-vision prism (between the direct-vision prism and the electrophoretic plate).

Accordingly, the migration lanes, the filter, the direct-vision prism, the condensing lens, the image intensifier and the two-dimensional detector are arranged in this order.

The migration lanes are made of a gel such as polyacrylamide gel as is well known, and the electrophoretic plate having the plurality of migration lanes is usually used. Ordinarily, the electrophoretic plate has a structure in which the gel is sandwiched between holders of quartz plates.

Usually, the output signal of the two-dimensional detector is applied to a monitor via a detector circuit and/or to an output device, such as plotter or cathode-ray tube, via the detector circuit as well as a computer. The applied signal is processed and analyzed.

As is well known, the image intensifier is a device wherein an optical image is focused on the photosensitive screen thereof and is converted into photoelectrons, and the photoelectrons are amplified as secondary electrons, which are projected on a fluorescent screen again, thereby to obtain a picture of clear densities. The device is a kind of amplifier for optical signals.

The wavelength dispersion electrophoresis apparatus of the present invention as described above has eliminated the difficulty of the prior art attributed to the use of the rotary filters. Moreover, since the apparatus of the present invention uses the direct-vision prism which differs from a conventional single prism and in which the plurality of prisms are combined, an optical path after emergence does not differ considerably from one before incidence, and only the dispersion based on the wavelengths is induced. Therefore, fluorescence images without a distortion can be focused on the image intensifier or the high-sensitivity two-dimensional detector by the use of the lens system and in the wavelength-dispersed form.

Assuming that the fluorescence images are taken in a horizontal direction, the fluorescence images resulting from the wavelength dispersion are arrayed in a vertical direction. The wavelengths are discriminated from positions in the vertical direction, while the positions of irradiated parts are discriminated from coordinates in the horizontal direction. The vertical dispersion expresses the differences of the base species labeled with the different fluorophores, while the horizontal positions reflect the differences of loaded positions and express the differences of the samples.

The present invention may well employ the techniques of known electrophoresis apparatuses of the fluorescence detection type except the measure for discriminating the wavelengths of the fluorescences, especially the adoption of the direct-vision prism and the entering direction of the exciting laser beam.

DESCRIPTION OF THE PREFERRED EMBODIMENTS

Now, embodiments of the present invention will be described with reference to the drawings.

Figure 1:
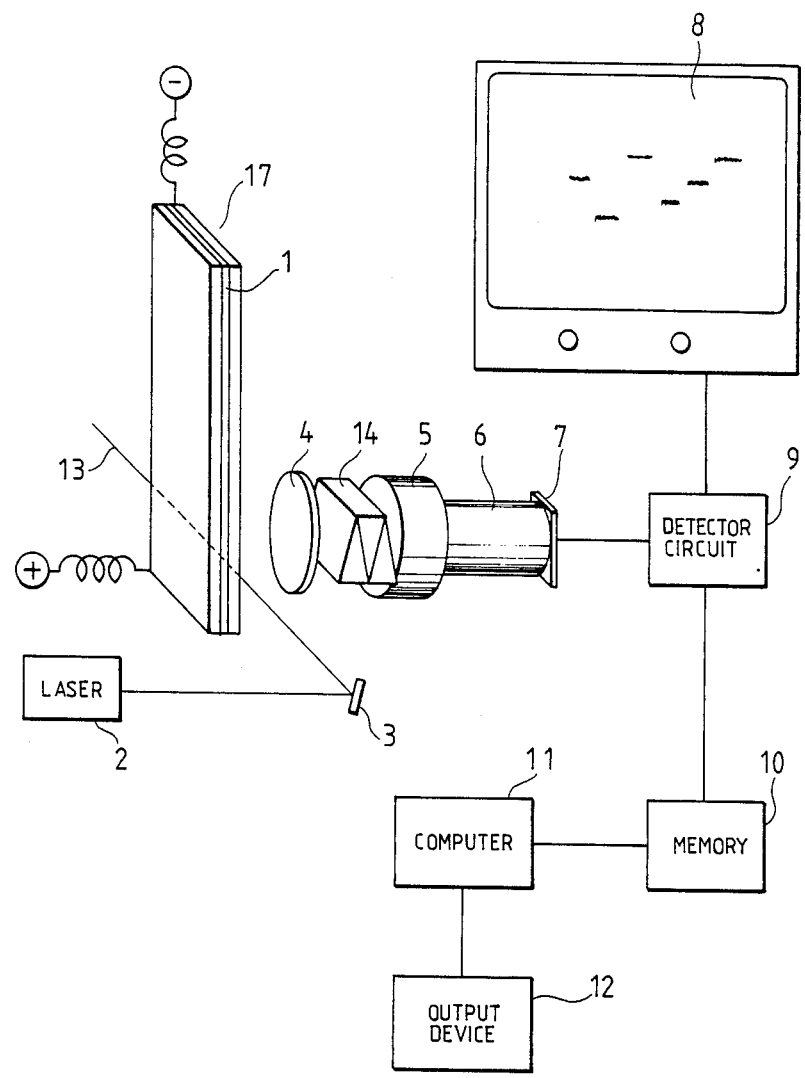
FIG. 1 is a schematic view showing the construction of a wavelength dispersion electrophoresis apparatus in an embodiment of the present invention.
Figure 2:
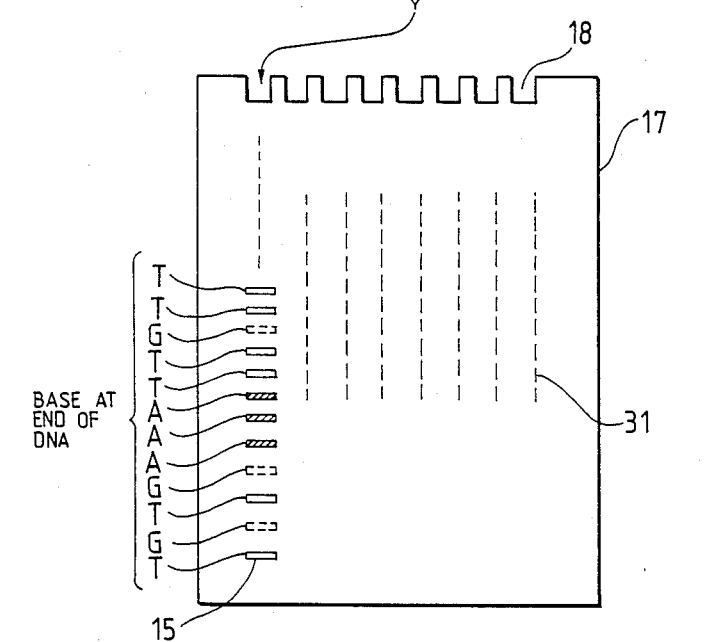
FIG. 2A is an explanatory diagram showing an example of the base sequence of DNA.
FIG. 2B is an explanatory diagram showing principles for determining the base sequence of the DNA.

FIG. 1 shows the construction of the whole apparatus. FIGS. 2A and 2B illustrate the principles of base sequence determination, and FIG. 3 the operating principle of a composite prism.

One end of DNA 16 (FIG. 2A) to have its sequence determined is labeled with a fluorophore $F_1$, and a group of fragments each of which has the base of adenine (A) at the other end ({A} Group) is prepared. Similar groups of fragments are also prepared for the other bases; cytosine (C), guanine (G) and thymine (T). Here, the kinds of labeling fluorophores are changed for the individual groups of fragments as being $F_2$, $F_3$ and $F_4$ for C, G and T, respectively. These groups of fragements ; {A} Group, {C} Group, {G} Group and {T} Group are put togehter, and the sample is loaded in a sample well 18 on an electrophoresis gel so as to be subjected to electrophoresis. One migration lane 31 is used for one sample. In this embodiment, a plurality of migration lanes 31 can be held in an electrophoretic plate 17, so that a large number of samples can be simultaneously measured. As illustrated in FIG. 2B, a shorter DNA fragment migrates faster. Therefore, when a place at a predetermined distance (20-30 cm in this embodiment) from the start point of the electrophoresis is irradiated with light thereby to observe fluorescences emitted from the DNA fragments passing the place, the lengths of the bases are found from flowing periods of time, and the base species at the other ends are found from fluorescence wavelengths.

The electrophoresis gel contains 3-8 wt.% of polyacrylamide, and it is 0.2 mm thick, 20 cm wide and 30 cm long. It is sandwiched between quartz plates. Although, in FIG. 2B, DNA bands 15 exist in only the migration lane 31 at the left end, DNA bands can exist in the respective migration lanes 31.

As the excitation light, a laser beam 13 (FIG. 1) is employed by way of example. The laser beam 13 is emitted from a laser 2 and is properly reflected by a mirror 3, whereupon it enters a gel plate 1 from the side thereof horizontally and substantially in parallel with the plane of the plate. A measurement region is a region which extends 10 cm in the horizontal direction on the electrophoretic plate.

Fluorescence images emitted from the gel and the fluorophores in the rectilinear portion irradiated by the excitation light as includes the plurality of migration lanes pass through a filter 4 for cutting the excitation light, and are subjected to wavelength dispersion by a direct-vision prism 14. The dispersed images are focused on an image intensifier 6 as irradiated region images by a focusing lens 5. The dispersed and intensified images are received by a two-dimensional detector 7, the horizontal positions of which express the coordinates of the irradiated portion and the vertical direction of which corresponds to the wavelength dispersion. Accordingly, fluorescence signals from one group of DNA fragments are received with one or several horizontal lines on the detector, and wavelength-dispersion fluorescence signals are obtained with at least four horizontal lines. These signals are applied to a detector circuit 9, and the situation of the signal detection can be observed on a monitor 8. In addition, signals from the detector circuit 9 can be processed and analyzed by a memory 10, a computer 11 and an output device 12.

Figure 3:
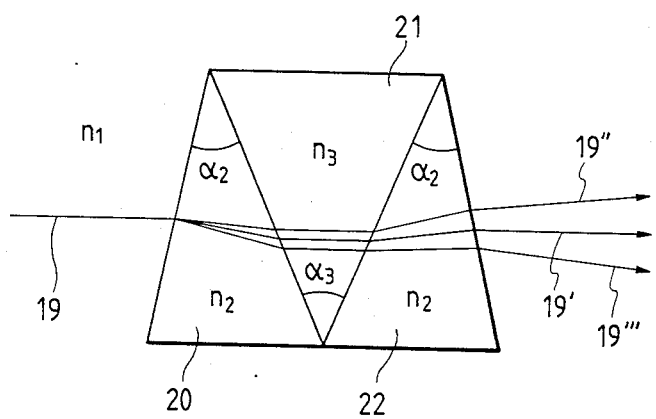
FIG. 3 is a sectional view showing a direct-vision prism for use in a wavelength dispersion electrophoresis apparatus in an embodiment of the present invention.

Next, there will be described an example in the case where a laser beam at an excitation wavelength of 488 nm was employed as the excitation light, while FITC (fluorescein isothiocyanate at an emission wavelength of 515 nm) and its isomers (at emission wavelengths of 535 nm, 555 nm and 575 nm) were used as the fluorophores. When, as illustrated in FIG. 3, prisms of refractive indices $n_2$ and $n_3$ are used in combination, the angular dispersion $$\frac{\partial U_{out}}{\partial \lambda}$$

of the angle of refraction dependent upon wavelengths is given by the following formula:

$$\frac{\partial U_{out}}{\partial \lambda} = \frac{2\alpha_2}{\lambda_F - \lambda_C} \left( \frac{n_{d2} - 1}{\nu_{d2}} - \frac{n_{d3} - 1}{\nu_{d3}} \cdot \frac{n_2 - n_1}{n_3 - n_1} \right)$$

where $U_{out}$ denotes the angle of deviation, $\lambda$ the wavelength, $\alpha_2$ the apical angle of each of the first prism 20 and the third prism 22, $n_2$ in the mean refractive index of each of the first and third prisms (the "mean refractive index" signifying a refractive index at the average wavelength of the four fluorescence wavelengths), $n_1$ the refractive index of air, and $n_3$ the mean refractive index of the second prism 21 and further, $n_{d2}$ denotes the $n_d$ value (the refractive index for the D-line at 587.6 nm) of the constituent glass of the first prism 20 and the third prism 22, $n_{d3}$ the $n_d$ value of the constituent glass of the second prism 21, $\nu_{d2}$ the $\nu_d$ value (the dispersion of the refractive index for the D-line) of the constituent glass of the first and third prisms, and $\nu_{d3}$ and $\nu_d$ value of the constituent glass of the second prism. $\lambda_F$, $\lambda_C$ and $\lambda_D$ (the wavelengths of the F-line, C-line and D-line) are 486.1 nm, 656.3 nm and 587.6 nm, respectively. Besides, the refractive index $n_1$ is 1 (unity).

When the apical angle $\alpha_2$ is set at 15° and "SFS1" and "FK5" are respectively employed as the materials of the first prism and the second prism, then the refractive index $n_2$ becomes 1.92, the refractive index $n_3$ becomes 1.4, and the apical angle $\alpha_3$ of the second prism 21 becomes:

$$\alpha_2 \cdot \frac{n_2 - n_1}{n_3 - n_1} \approx 34.5°$$

In addition, $\nu_{d2} = 21$, $n_{d2} = 1.92$, $\nu_{d3} = 70$ and $n_{d3} = 1.4$ hold. Therefore, the following is calculated:

$$\frac{\partial U_{out}}{\partial \lambda} = \frac{2 \times 0.262}{-0.1702} \left( \frac{0.92}{21} - \frac{0.92}{70} \right)$$

$$= -0.095$$

Here, it is assumed that the difference of the wavelengths is $\Delta\lambda = 20$ nm and that the distance between the lens and the lens image is $L = 60$ mm. Then, the dispersion $\Delta l$ on the image intensifier becomes:

$$\Delta l = 0.095 \cdot \Delta\lambda \cdot L$$
$$= 0.11 \text{(mm)}$$

That is, the dispersion of 0.11 mm is attained on the image intensifier. In an example in which a still greater dispersion was required, $\alpha_2 = 30°$ and $L = 100$ mm were set to render the dispersion 0.36 mm greater, whereby wavelengths could be satisfactorily discriminated.

Incidentally, the positional resolution of the image intensifier is about 0.03 mm.

Numeral 19 in FIG. 3 indicates an incident beam, and numerals 19', 19" and 19''' indicate outgoing beams having wavelength of D-line, wavelength longer than D-line and wavelength shorter than D-line respectively.

According to the wavelength dispersion electrophoresis apparatus of the present invention, wavelength dispersion can be performed without greatly changing an optical path, so that fluorescence images can be measured through the wavelength dispersion without being distorted. The system of the invention need not receive unequal wavelengths alternately with the rotary filters as in the prior art and can receive the fluorescences of individual wavelengths in sufficient amounts over the whole measurement time by the use of a simple mechanism, so that a very high sensitivity is attained.

What is claimed is:

1. In an electrophoresis apparatus having means for electrophoretically separating a sample group which consists of samples labeled with at least two kinds of fluorophores, excitation means for exciting the fluorophore which has labeled the sample, thereby causing it to emit fluorescence, and detection means for detecting the emitted fluorescence; a wavelength dispersion electrophoresis apparatus characterized in that a composite prism (14) in which a plurality of unit prisms made of different materials are combined and which disperses the fluorescences at respective fluorescence wavelengths is disposed in front of said detection means.

2. A wavelength dispersion electrophoresis apparatus as defined in claim 1, wherein the electrophoresis separation means is configured of a plurality of migration lanes (31) which are set in parallel, said excitation means is constructed of excitation light (13) which intersects all of said migration lanes (31) and which enters perpendicularly to said migration lanes (31), said detection means is constructed of a two-dimensional detector (7), and said composite prism (14) and said detection means are so arranged that the wavelength dispersion occurs in a direction perpendicular to a fluorescence image.

3. A wavelength dispersion electrophoresis apparatus as defined in claim 2, wherein a filter (4) for cutting the excitation light is disposed in front of said composite prism.

4. A wavelength dispersion electrophoresis apparatus comprising (i) an electrophoretic plate (17) which includes a plurality of migration lanes (31) for electrophoresis of a sample group consisting of samples labeled with at least two kinds of fluorophores, (ii) a filter (4) which cuts excitation light, (iii) a composite prism (14) in which a plurality of unit prisms made of different materials are combined, (iv) a condensing lens (5), (v) an image intensifier (6), and (vi) a two-dimensional fluorescence detector (7), the constituents (i) thru (vi) being disposed in this order, and means for causing a laser beam (13) as said excitation light to enter so as to intersect all of said migration lanes (31) substantially orthogonally.

5. A wavelength dispersion electrophoresis apparatus as defined in claim 4, wherein said laser beam (13) is a collimated beam whose section is circular and has a diameter of at most 0.3 mm in a measurement region of said electrophoretic plate (17).

* * * * *